United States Patent

Babin et al.

[11] Patent Number: 5,135,951
[45] Date of Patent: Aug. 4, 1992

[54] 3-(2-CYANO-2-HALO-ETHENYL)-2,2-DIMETHYL-CYCLOPROPANECARBOXYLATES

[75] Inventors: Didier Babin, Montigny; Marc Benoit, Roquevaire; Jean-Pierre Demoute, Neuilly Plaisance; Jean Tessier, Vincennes, all of France

[73] Assignee: Roussel Uclaf, Paris, France

[21] Appl. No.: 661,383

[22] Filed: Feb. 26, 1991

[30] Foreign Application Priority Data

Feb. 27, 1990 [FR] France ................. 90-02406

[51] Int. Cl.⁵ ................. C08C 255/31; A01N 37/34
[52] U.S. Cl. ................. 514/521; 558/407
[58] Field of Search ................. 558/407; 514/521

[56] References Cited

U.S. PATENT DOCUMENTS

| | | | |
|---|---|---|---|
| 4,565,822 | 1/1986 | Tessier et al. | 558/407 X |
| 4,602,038 | 7/1986 | Tessier et al. | 558/407 X |
| 4,670,464 | 6/1987 | Doyle et al. | 558/407 X |
| 4,681,969 | 7/1987 | Williams et al. | 558/407 |
| 4,732,903 | 3/1988 | Martel et al. | 558/407 X |
| 4,849,449 | 7/1989 | Tessier et al. | 558/407 X |
| 4,874,887 | 10/1989 | Jung et al. | 558/407 X |
| 4,879,302 | 11/1989 | Tessier et al. | 558/407 X |
| 4,920,231 | 4/1990 | Bonin et al. | 558/407 X |

*Primary Examiner*—Joseph Paul Brust
*Attorney, Agent, or Firm*—Bierman and Muserlian

[57] ABSTRACT

All stereoisomeric forms and mixtures thereof of a compound of the formula

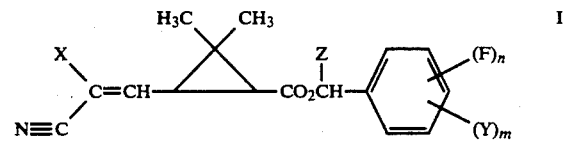

wherein the cyclopropane copula has (1R, cis) or (1R, trans) structure, the geometry of the double bond carried by the 3-carbon atom is (E) or (Z), X is halogen, Z is selected from the group consisting of hydrogen, methyl, —CN and —C≡CH, n is an integer from 1 to 5, m represents the number 5-n, Y is selected from the group consisting of hydrogen, halogen, —CH₂—CN, —OH, optionally unsaturated alkyl of 1 to 8 carbon atoms unsubstituted or substituted with at least one halogen, —CN, —COOAlk, —COAlk, —(CH₂)$_m'$OAlk, —(CH₂)$_m'$—S—Alk, —(CH₂)$_m'$—N(Alk)₂, —Si(Alk)₃, —OAr and (CH₂)$_m'$—Ar, m' is 0, 1,2,3 or 4, Alk is optionally unsaturated alkyl of 1 to 8 carbon atom unsubstituted or substituted with at least one halogen and Ar is aryl of 6 to 14 carbon atoms and the Ys identical or different may be on any position of the phenyl having pesticidal properties.

22 Claims, No Drawings

3-(2-CYANO-2-HALO-ETHENYL)-2,2-DIMETHYL-CYCLOPROPANECARBOXYLATES

STATE OF THE ART

Pertinent related prior art includes U.S. Pat. No. 4,565,822.

OBJECTS OF THE INVENTION

It is an object of the invention to provide the novel compounds of formula I and a process for their preparation.

It is another object of the invention to provide novel pesticidal compositions and a method of combatting pests, particularly insects.

These and other objects and advantages of the invention will become obvious from the following detailed description.

THE INVENTION

The novel compounds of the invention are all stereoisomeric forms and mixtures thereof of a compound of the formula

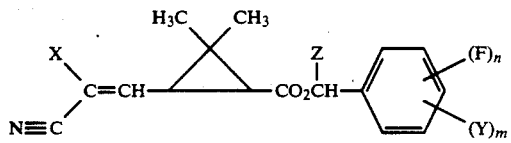

wherein the cyclopropane copula has (1R, cis) or (1R, trans) structure, the geometry of the 3-carbon atoms is (E) or (Z), X is halogen, Z is selected from the group consisting of hydrogen, methyl, —CN and —C≡CH, n is an integer from 1 to 5, m represents the number 5-n, Y is selected from the group consisting of hydrogen, halogen, —CH$_2$—CN, —OH, optionally unsaturated alkyl of 1 to 8 carbon atoms unsubstituted or substituted with at least one halogen, —CN, —COOAlk, —COAlk, —(CH$_2$)$_{m'}$—OAlk, —(CH$_2$)$_{m'}$—S—Alk, —(CH$_2$)$_{m'}$—N(Alk)$_2$, —Si(Alk)$_3$, —OAr and —(CH$_2$)$_{m'}$—Ar, m' is 0, 1, 2, 3 or 4, Alk is optionally unsaturated alkyl of 1 to 8 carbon atoms unsubstituted or substituted with at least one halogen and Ar is aryl of 6 to 14 carbon atoms and the Ys identical or different may be in any position of the phenyl.

X is preferably fluorine, chlorine or bromine and if Y is halogen, it is preferably chlorine or bromine; X is preferably fluorine.

When Y is alkyl, it is preferably methyl, ethyl, propyl, isopropyl, n-butyl or tert-butyl. When Y is an unsaturated alkyl, it is an ethylene such as ethenyl, propenyl or propadienyl or an acetylene such as ethynyl or propynyl. When Y is alkyl substituted by at least one functional group they are preferably halogens such as fluorine or bromine and Y can be CF$_3$. When Y is (CH$_2$)$_{m'}$—O-alkyl or (CH$_2$)$_{m'}$—S-alkyl, it is preferably —OCH$_3$ or —SCH$_3$. When Y is O-Aryl or (CH$_2$)$_{m'}$-Aryl, Aryl is preferably phenyl.

Among the preferred compounds of the invention are those of the formula

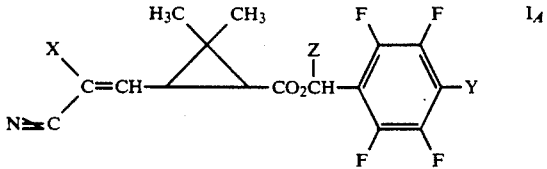

in which X, Y and Z have the above definitions, those wherein Z is hydrogen, those wherein Y is alkyl of 1 to 4 carbon atoms, especially methyl or ethyl or alkenyl or alkynyl of 2 to 4 carbon atoms or hydrogen, those wherein the cyclopropane copula is of (1R, cis) structure and those wherein the double bond is of (E) geometry and especially the compound of Example 1.

The process of the invention for the preparation of the compounds of formula I comprises reacting a compound of the formula

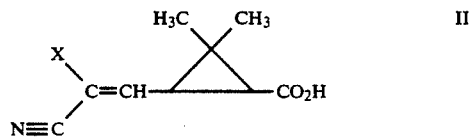

wherein X has the above definition or a derivative of the acid with an alcohol of the formula

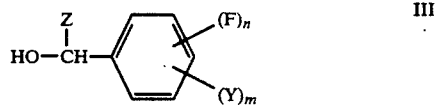

in which X, Y, Z, m and n have the above definitions or a functional derivative of the alcohol to obtain the corresponding compound of formula I.

The acids of formula II are known products which can be prepared as indicated in European Patent No. 0,133,406. The alcohols of formula III are compounds which are known generally and they can be prepared for example by the processes described in European Patent Application No. 0,031,199, in U.S. Pat. Nos. 4,370,346, 4,405,640 in English Patent No. 2,171,994, in British Crop Protection Conference Pest and Disease 1986 page 199 or also in the European Patent Application No. 0,281,439.

The pesticidal compositions of the invention are comprised of a pesticidally effective amount of at least one compound of formula I and an inert carrier. The compositions are useful against parasites of vegetation whether sub-soil or super-soil parasites and parasites of warm-blooded animals and the premises and can be used against insects, nematodes and acarids of vegetation and warm-blooded animals.

The compositions may also be used to combat insects and other parasites of the soil, for example, coleoptera such as DIABROTICA, click beetles and cockchafer grubs, Myriapoda such as scutigeridae and blanjules, Diptera such as gall midges and Lepidoptera such as owlet moths. They are used at doses of between 10 g and 300 g of active material per hectare.

The compositions can also be used to combat insects in premises, notably to combat flies, mosquitoes and cockroaches. Moreover, the compositions are photostable and less toxic to mammals. All these properties make the compositions which correspond perfectly to the demands of the modern agrochemical industry as they allow the protection of crops while preserving the environment.

The compositions can also be used to combat parasitic acaridae and nematodes of vegetation and can also be used to combat parasitic acaridae of animals, to combat, for example, ticks and notably ticks of the Boophilus species, those of the Hyalomnia species, those of the Amblyomnia species and those of the Rhipicephalus species or to combat all sorts of mites and notably the sarcoptic mite, the psoroptic mite and the chorioptic mite.

Particularly preferred are insecticide compositions containing as active ingredient at least one of the products defined above.

The compositions of the invention are prepared by the usual processes of the agrochemical industry or the veterinary industry or the animal feed products industry. These compositions can be in the form of powders, granules, suspensions, emulsions, solutions, aerosol solutions, combustible strips, baits or other preparations usually employed for the use of this type of compound.

In addition to the active ingredient, the compositions may contain a vehicle and/or a nonionic surface active agent, ensuring, moreover, a uniform dispersion of the components of the mixture. The vehicle used can be a liquid such as water, alcohol, hydrocarbons or other organic solvents, a mineral, animal or vegetable oil, a powder such as talc, clays, silicates, kieselguhr or a combustible solid.

The insecticide compositions of the invention contain preferably 0.005% to 10% by weight of active material. According to an advantageous operating method, for use in premises, the compositions of the invention are used in the form of fumigant compositions.

The compositions of the invention can then be advantageously composed of, for the non-active part, a combustible insecticide serpentine (or coil), or also an incombustible fibrous substrate. In the latter case, the fumigant obtained after incorporation of the active ingredient is placed on a heating apparatus such as an electric emanator.

In the case where an insecticide serpentine is used, the inert support can be comprised of Pyrethrum marc, Tabu powder (or Machilus thumbergii leaf powder), Pyrethrum stem powder, cedar leaf powder, sawdust (such as pine sawdust), starch and coconut shell powder. The dose of active ingredient can then be, for example, 0.03 to 1% by weight. In the case where an incombustible fibrous support is used, the dose of active ingredient can then be 0.03 to 95% by weight.

The compositions of the invention for use in premises can also be obtained by preparing a sprayable oil based on the active ingredient, this oil soaking a lamp wick and then being set alight. The concentration of active ingredient incorporated in the oil is preferably 0.03 to 95% by weight.

The acaricide and nematocide compositions contain as active ingredient at least one of the products of formula I, as defined above. The insecticide compositions of the invention, as acaricide and nematocide compositions, can optionally have other pesticide agents added to them. The acaricide and nematocide compositions can be presented preferably in the form of powder, granules, suspensions, emulsions or solutions.

For acaricide use, wettable powders are preferably used for foliar spraying and contain 1 to 80% of active ingredient or liquids for foliar spraying containing 1 to 500 g/l of active ingredient. Powders for foliar dusting containing 0.05% to 3% of active ingredient can also be used.

For nematocide use, liquids for soil treatment containing 300 to 500 g/l of active ingredient are preferably used. The acaricide and nematocide compositions of the invention are used, preferably, at doses comprised between 1 and 100 g of active ingredient per hectare.

To increase the biological activity of the products of the invention, there can be added standard synergists used in such cases such as 1-(2,5,8-trioxadodecyl)-2-propyl-4,5-methylenedioxy benzene (or piperonyl butoxide) or N-(2-ethyl-heptyl)-bicyclo-[2,2-1]-5-heptene-2,3-dicarboximide, or piperonyl-bis-2-(2'-n-butoxy-ethoxy) ethylacetal or (tropital).

The compounds of formula I show an excellent general tolerance, and therefore are useful to combat affections caused by ticks and mites in humans and animals, especially to combat lice as a preventative or curative and to combat mites.

The compositions of the invention can be administered externally by spraying, by shampooing, by bathing or painting on. The compositions for veterinary use can also be administered by painting the dorsal spine by the "pour-on" method.

It can also be mentioned that the compositions of the invention can be used as biocides or a growth regulators.

Also a subject of the invention are combinations endowed with insecticide, acaricide or nematocide activity, characterized in that they contain as active ingredient at least one of the compounds of formula I and at least one of the pyrethrinoid esters chosen from the group consisting of the esters of allethrone, of 3,4,5,6-tetrahydrophthalimidomethyl alcohol, of 5-benzyl-3-furyl methyl alcohol, of 3-phenoxybenzyl alcohol and of α-cyano-3-phenoxybenzyl alcohols with chrysanthemic acids, by the esters of 5-benzyl-3-furyl methyl alcohol with 2,2-dimethyl-3-(2-oxo-3-tetrahydrothiophenylidenemethyl)-cyclopropane-1-carboxylic acids, by the esters of 3-phenoxybenzyl alcohol and of α-cyano-3-phenoxybenzyl alcohols with 2,2-dimethyl-3-(2,2-dichlorovinyl)-cyclopropane-1-carboxylic acids, by the esters of α-cyano-3-phenoxybenzyl alcohols with 2,2-dimethyl-3-(2,2-dibromovinyl)-cyclopropane-1-carboxylic acids, by the esters of 3-phenoxybenzyl alcohols with 2-parachlorophenyl-2-isopropyl acetic acid, by the esters of allethrolones, of 3,4,5,6-tetrahydrophthalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane-1-carboxylic acids, in which "halo" reprsents a fluorine, chlorine or bromine atom, it being understood that the compounds I can exist in all their possible streoisomer forms as well as the acid and alcohol copulas of the above pyrethrinoid esters.

The novel method of the invention for combatting parasites comprises contacting parasites with a parasitically effective amount of at least one compound of formula I. The method is particularly effctive against insects.

In the following examples, there are described several preferred embodiments to illustrate the invention. However, it should be understood that the invention is not intended to be limited to the specific embodiments.

EXAMPLE 1

2,3,5,6-tetrafluoro-4-methyl-benzyl [1R-[1α,3α(E)]]-3-(2-cyano-2-fluoroethenyl)-2,2-dimethyl cyclopropane carboxylate A solution of 1.27 g of 3-[2-cyano-2-fluoroethenyl]-cyclopropane carboxylic acid, 13 ml of methylene chloride, 1.36 g of (2,3,5,6-tetrafluoro-4-methyl-phenyl) methanol and 50 mg of 4-dimethylamino-pyridine was cooled to 0° C. and 1.46 g of dicyclohexylcarbodiimide and 5 ml of methylene chloride were added dropwise. The suspension was stirred for 17 hours at 20° C. to obtain 2.32 g of crude product which was chromatographed on silica and eluted with a hexane ethyl acetate mixture (9-1). After evaporating to dryness, 2.19 g of the desired product with a specific rotation of $[\alpha]_D = +63.5° \pm 2.5°$ (c=0.4% in CHCl$_3$) were obtained.

Using the procedure of Example 1, the appropriate acids were reacted to obtain the following products:

EXAMPLE 2

2,3,5,6-tetraluoro-4-(1,2-propanedienyl)-benzyl [1R-[1α,3α(E)]]-3-(2-cyano-2-fluoro-ethenyl)-2,2-dimethyl cyclopropanecarboxylate with a specific rotation of $[\alpha]_D = 30° \pm 2°$ (c=0.45% in CHCl$_3$).

EXAMPLE 3

2,3,5,6-tetrafluoro-4-methoxy-benzyl [1R-[1α, 3α-(E)]]-3-(2-cyano-2-fluoro-ethenyl)-2,2-dimethyl cyclopropanecarboxylate with a specific rotation of $[\alpha]_D = 36.5° \pm 2°$ (c=0.7% in CHCl$_3$).

EXAMPLE 4

2,3,5,6-tetrafluoro-benzyl [1R-[1α,3α(E)]]-3-(2-cyano-2-fluoro-ethenyl)-2,2-dimethyl cyclopropanecarboxylate with a specific rotation of $[\alpha]_D = 52.5° \pm 2.5°$ (c=0.6% in CHCl$_3$).

EXAMPLE 5

2,3,5,6-tetrafluoro-4-methyl-benzyl [1R-[1α,3α(Z)]]-3-(2-cyano-2-fluoro-ethenyl)-2,2-dimethyl cyclopropanecarboxylate melting at 93.6° C.

EXAMPLE 6

2,3,5,6-tetrafluoro-4-ethynyl-benzyl [1R-[1α,3α(E)]]-3-(2-cyano-2-fluoro-ethenyl)-2,2-dimethyl-cyclopropanecarboxylate melting at 47.5° C. and with a specific rotation of $[\alpha]_D = +39° \pm 1.5°$ (c=1% in CHCl$_3$).

EXAMPLE 7

2,3,5,6-tetrafluoro-4-ethenyl-benzyl [1R-[1α,3α(E)]]-3—(2-cyano-2-fluoro-ethenyl)-2,2-dimethyl cyclopropanecarboxylate.

EXAMPLE 8

2,3,5,6-tetrafluoro-4-ethyl-benzyl [1R-[1α, 3α(Z)]]-3-(2-cyano-2-fluoro-ethenyl)-2,2-dimethyl-cyclopropanecarboxylate

EXAMPLE 9

2,3,5,6-tetrafluoro-4-ethyl-benzyl [1R-[1α, 3α(E)]]-3-(2-cyano-2-fluoro-ethenyl)-2,2-dimethyl-cyclopropanecarboxylate.

EXAMPLE 10

2,3,5,6-tetrafluoro-4-(2-propynyl)-benzyl [1R-[1α, 3α(E)]]-3-(2-cyano-2-fluoro-ethenyl)-2,2-dimethyl cyclopropanecarboxylate.

EXAMPLE 11

2,3,5,6-tetrafluoro-4-(2-propynyl)-benzyl [1R-[1α, 3α(Z)]]-3-(2-cyano-2-fluoro-ethenyl)-2,2-dimethyl cyclopropanecarboxylate.

EXAMPLE 12

2,3,5,6-tetrafluoro-4-(methoxymethyl)-benzyl [1R-[1α,3α(E)]]-3-(2-cyano-2-fluoro-ethenyl)-2,2-dimethyl cyclopropanecarboxylate with a specific rotation of $[\alpha]_D = +43° \pm 2.5°$ (c=0.5% in toluene).

EXAMPLE 13

2,3,5,6-tetrafluoro-4-(methoxymethyl)-benzyl [1R-[1α,3α(Z)]]-3-(2-cyano-2-fluoro-ethenyl)-2,2-dimethyl cyclopropanecarboxylate with a specific rotationof $[\alpha]_D = -30° \pm 2.5°$ (c=0.4% in toluene).

EXAMPLE 14

2,3,5,6-tetrafluoro-4-(2-propenyl)-benzyl [1R-[1α,3α(E)]]-3-(2-cyano-2-fluoro-ethenyl)-2,2-dimethyl cyclopropanecarboxylate.

EXAMPLE 15

Pentafluoro-benzyl [1R-[1α,3α(E)]]-3-(2-cyano-2-fluoro-ethenyl)-2,2-dimethyl cyclopropanecarboxylate with a specific rotation of $[\alpha]_D = +39° \pm 2°$ (c=0.8% in CHCl$_3$).

EXAMPLE 16

Pentafluoro-benzyl [1R-[1α,3α(Z)]]-3-(2-cyano-2-fluoro-ethenyl)-2,2-dimethyl cyclopropanecarboxylate with a specific rotation of $[\alpha]_D - 53° \pm 1.5°$ (c=1% in CHCl$_3$).

EXAMPLE 17

Preparation of a soluble concentrate

A homogeneous mixture was prepared containing:
Product of Example 1: 0.25 g
Piperonyl butoxide: 1.00 g
Tween 80: 0.25 g
Topanol A: 0.1 g
Water: 98.4 g

EXAMPLE 18

Preparation of an emulsifiable concentrate

The following were intimately mixed:
Product of Example 2: 0.015 g
Piperony butoxide: 0.5 g
Topanol A: 0.1 g
Tween 80: 3.5 g
Xylene: 95.885 g

EXAMPLE 19

Preparation of an emulsifiable concentrate

A homogeneous mixture was prepared containing:
Product of Example 1: 1.5 g
Tween 80: 20.00 g
Topanol A: 0.1 g
Xylene: 78.4 g

EXAMPLE 20

Preparation of a fumigant composition

The following were mixed together in a homogeneous manner:
Product of Example 1: 0.25 g
Tabu powder: 25.00 g
Cedar leaf powder: 40.00 g
Pine sawdust: 33.75 g
Brilliant green: 0.5 g
p-Nitrophenol: 0.5 g

BIOLOGICAL STUDY

A. Knock-down effect on the household fly

The test insects were 4 days old female household flies and the test was carried out by direct spraying in a Kearns and March chamber at a concentration of 0.10 g/l using a mixture of acetone (5%) and Isopar L (petroleum solvent) as solvent (quantity of solvent used 2 ml per second). 50 insects were used per treatment and checks were carried out every minute up to 10 minutes, then at 15 minutes and the $KT_{50}$ was determined by the usual methods. The experimental results are summarized in the following table:

| Compounds | $KT_{50}$ in mn |
|---|---|
| EXAMPLE 1 | 4.0 |
| EXAMPLE 3 | 3.6 |
| EXAMPLE 4 | 3.6 |
| EXAMPLE 5 | 6.6 |
| EXAMPLE 6 | 3.9 |
| EXAMPLE 7 | 5.7 |
| EXAMPLE 8 | 4.2 |
| EXAMPLE 9 | 6.2 |
| EXAMPLE 10 | 1.3 |
| EXAMPLE 11 | 1.2 |
| EXAMPLE 12 | 4.2 |
| EXAMPLE 13 | 1.7 |

B) Lethal effect on *Spodoptera littoralis* larvae

The tests were carried out by topical application of an acetone solution on the dorsal thorax of the larvae using an Arnold miro-manipulator and 15 larvae were used per dose of the test product. The larvae were fourth-stage larvae, that is to say aged about 10 days having been reared at 24° C. and 65% relative humidity. After treatment, the individuals were placed on an artificial nutritive medium (Poitout medium) and the mortality check was carried out 48 hours after treatment. The experimental results are summarized in the following table:

| Compounds | $LD_{50}$ in ng/insect |
|---|---|
| EXAMPLE 1 | 48.3 |
| EXAMPLE 5 | 35.6 |
| EXAMPLE 6 | 69.9 |
| EXAMPLE 7 | 70.8 |
| EXAMPLE 8 | 15.3 |
| EXAMPLE 9 | 51.9 |
| EXAMPLE 10 | 12.9 |
| EXAMPLE 11 | 2.5 |
| EXAMPLE 12 | 54.7 |
| EXAMPLE 13 | 21.6 |

C. Activity on Diabrotica

The test insects were final-stage larvae of Diabrotica and a 9 cm disc of filter paper placed at the bottom of a Petri dish was treated with 2 ml of an acetone solution. After drying, 10 larvae per dose were deposited and the mortality check was carried out 24 hours after treatment. The lethal dose 100 ($LD_{100}$) expressed in, mg/liter was determined. The results are the following:
Product of Example 1: 0.6
Product of Example 3: 2.5
Product of Example 4: 1.25
Product of Example 6: 5
Product of Example 7: 5
Product of Example 8: 5
Product of Example 9: 1.25
Product of Example 10: 0.6
Product of Example 11: 1.25

Various modifications of the products and methods of the invention may be made without departing from the spirit or scope thereof and it is to be understood that the invention is intended to be limited only as defined in the appended claims.

What we claim is:

1. All stereoisomeric forms and mixtures thereof of a compound of the formula

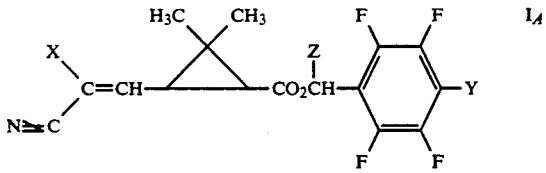

wherein the cyclopropane copula has (1R, cis) or (1R, trans) structure, the geometry of the double bond carried by the 3-carbon atom is (E) or (Z), X is halogen, Z is selected from the group consisting of hydrogen, emthyl, —CN, and —C≡CH, Y is selected from the group consisting of alkenyl and alkynyl of up to 8 carbon atoms.

2. A compound of claim 1 wherein Y is fluorine.
3. A compound of claim 1 wherein Z is hydrogen.
4. A compound of claim 1 wherein Y is alkenyl or alkynyl of 2 to 4 carbon atoms.
5. A compound of claim 1 wherein the cyclopropane copula has (1R, cis) structure.
6. A compound of claim 1 wherein the double bond has (E) geometry.
7. A compound of claim 1 which is 2,3,5,6-tetrafluoro-4-(2-propynyl) [1R-[1α,3α(E)]]-3-(2-cyano-2-fluoro-ethenyl)-2,2-dimethyl-cyclopropanecarboxylate.
8. An insecticidal composition comprising an insecticidally effective amount of a compound of claim 1 and an inert carrier.
9. A composition of claim 8 wherein X is fluorine.
10. A composition of claim 8 wherein Z is hydrogen.
11. A composition of claim 8 wherein Y is alkenyl or alkynyl of 2 to 4 carbon atoms.
12. A composition of claim 8 wherein the cyclopropane copula has (1R,cis) structure.
13. A composition of claim 8 wherein the double bond has (E) geometry.
14. A composition of claim 8 wherein the compound is 2,3,5,6-tetrafluoro-b 4-(2-propynyl)-benzyl [1R-[1α,-3α(E)]]-3—(2-cyano-2-fluoroethenyl)-2,2-dimethyl-cyclopropanecarboxylate.
15. A method of combatting insects comprising contacting insects with an insecticidally effective amount of a compound of claim 1.
16. A method of claim 15 wherein X is fluorine.

17. A method of claim 15 wherein Z is hydrogen.

18. A method of claim 15 wherein Y is alkenyl or alkynyl of 2 to 4 carbon atoms.

19. A method of claim 15 wherein the cyclopropane copula has (1R, cis) structure.

20. A method of claim 15 wherein the double bond has (E) geometry.

21. A method of claim 15 wherein the compound is 2,3,5,6-tetrafluoro-4-(2-propynyl)-benzyl [1R-[1α, 3α-(E)]]-3-(2-cyano-2-fluoroethenyl)-2,2-dimethyl-cyclopropanecarboxylate.

22. The method of claim 15 wherein the insects are Diabrotica.

* * * * *